US010836659B2

(12) United States Patent
Giguere

(10) Patent No.: US 10,836,659 B2
(45) Date of Patent: Nov. 17, 2020

(54) CHEMICAL CONTROL SYSTEMS AND METHODS FOR CONTROLLING DISINFECTANTS

(71) Applicant: UGSI Solutions, Inc., Poway, CA (US)

(72) Inventor: Robin Giguere, Piedmont, CA (US)

(73) Assignee: UGSI Solutions, Inc., Poway, CA (US)

( * ) Notice: Subject to any disclaimer, the term of this patent is extended or adjusted under 35 U.S.C. 154(b) by 184 days.

(21) Appl. No.: 16/135,590

(22) Filed: Sep. 19, 2018

(65) Prior Publication Data

US 2019/0084849 A1    Mar. 21, 2019

Related U.S. Application Data

(60) Provisional application No. 62/560,252, filed on Sep. 19, 2017.

(51) Int. Cl.
*C02F 1/00*   (2006.01)
*C02F 1/68*   (2006.01)
(Continued)

(52) U.S. Cl.
CPC .............. *C02F 1/686* (2013.01); *C02F 1/008* (2013.01); *C02F 1/76* (2013.01); *G01N 33/182* (2013.01);
(Continued)

(58) Field of Classification Search
CPC .. C02F 1/008; C02F 1/686; C02F 1/76; C02F 2209/003; C02F 2209/005; C02F 2209/04;
(Continued)

(56) References Cited

U.S. PATENT DOCUMENTS 4,406,582 A    9/1983  LaGrange
4,435,291 A    3/1984  Matsko
(Continued)

FOREIGN PATENT DOCUMENTS

WO        0238507 A1    5/2002
WO    2009055093 A1    4/2009
(Continued)

OTHER PUBLICATIONS

Steininger, "PPM or ORP: Which Should Be Used?", Swimming Pool Age & Spa Merchandiser, Nov. 1985.
(Continued)

*Primary Examiner* — Lucas A Stelling
(74) *Attorney, Agent, or Firm* — The Webb Law Firm

(57) ABSTRACT

A method of automatically controlling chloramine concentration in a body of water contained in a reservoir includes: (a) determining residual chloramine concentration in a water sample obtained from the body of water; (b) determining at least one of the following when the residual chloramine concentration is below a predetermined target chloramine concentration level: (i) an average rate of change in total chlorine concentration; and (ii) an average rate of change in oxidation-reduction potential; and (c) automatically engaging a supply of ammonia and a supply of chlorine to add both ammonia and chlorine to the body of water at a weight ratio of chlorine to ammonia of 5:1 or less when the average rate of change in total chlorine concentration is below a set rate of change and/or the average rate of change in oxidation-reduction potential is above a set rate of change.

20 Claims, 7 Drawing Sheets

(51) Int. Cl.
   *C02F 1/76*   (2006.01)
   *G01N 33/18*  (2006.01)
(52) U.S. Cl.
   CPC .. *C02F 2209/003* (2013.01); *C02F 2209/005* (2013.01); *C02F 2209/04* (2013.01); *C02F 2209/14* (2013.01); *C02F 2209/29* (2013.01); *C02F 2303/04* (2013.01)
(58) Field of Classification Search
   CPC .............. C02F 2209/14; C02F 2209/29; C02F 2303/04; G01N 33/182
   See application file for complete search history.

(56) References Cited

U.S. PATENT DOCUMENTS

| | | |
|---|---|---|
| 4,752,740 A | 6/1988 | Steininger |
| 5,547,584 A | 8/1996 | Capehart |
| 5,854,744 A | 12/1998 | Zeng et al. |
| 5,934,877 A | 8/1999 | Harman |
| 6,143,184 A | 11/2000 | Martin et al. |
| 6,315,950 B1 | 11/2001 | Harp et al. |
| 6,702,551 B2 | 3/2004 | Kikuchi et al. |
| 6,716,354 B2 | 4/2004 | Rosenblatt et al. |
| 7,300,592 B2 | 11/2007 | Iseki et al. |
| 7,488,151 B2 | 2/2009 | Harman |
| 7,862,302 B2 | 1/2011 | Harman |
| 8,051,383 B2 | 11/2011 | McCampbell et al. |
| 8,887,556 B2 | 11/2014 | Silveri |
| 9,039,902 B2 | 5/2015 | Simmons et al. |
| 2003/0232447 A1 | 12/2003 | Kahle |
| 2005/0137118 A1 | 6/2005 | Silveri |
| 2006/0096930 A1 | 5/2006 | Beardwood |
| 2006/0124558 A1 | 6/2006 | Kouame |
| 2009/0320570 A1 | 12/2009 | Wiese |
| 2011/0210078 A1 | 9/2011 | Simmons et al. |
| 2012/0021062 A1 | 1/2012 | Gupta et al. |
| 2015/0203388 A1 | 7/2015 | Gotthardt et al. |
| 2015/0329391 A1 | 11/2015 | Garusi et al. |
| 2016/0362318 A1 | 12/2016 | Simmons |
| 2016/0376166 A1 | 12/2016 | Lawryshyn et al. |
| 2017/0190601 A1 | 7/2017 | Augustine et al. |
| 2017/0203974 A1 | 7/2017 | Riedl et al. |
| 2017/0253502 A1 | 9/2017 | Bejan et al. |
| 2018/0282882 A1 | 10/2018 | Boal et al. |
| 2018/0346358 A1* | 12/2018 | Fritz ................ C02F 1/008 |

FOREIGN PATENT DOCUMENTS

| | | |
|---|---|---|
| WO | 2012010864 A1 | 1/2012 |
| WO | 2013009106 A2 | 1/2013 |
| WO | 2015179919 A1 | 12/2015 |
| WO | 2015187982 A1 | 12/2015 |

OTHER PUBLICATIONS

Yu et al., "Determination of chlorine demand in water and wastewater chlorination by oxidation-reduction potential", Water Science and Technology: Water Supply, 2003, pp. 313-320, vol. 3, No. 1-2.
"Oxidation Reduction Potential (ORP)/Redox and Free Chlorine", Myron L Company, 2012.
Baribeau, "Nitrification in Distribution Systems: Effects, Causes, and Control", AWWA 2015 Operator Symposium, 2015, AQUAlity Engineering, Inc., Ontario, California.
Turner, "Slope Filtering: An FIR Approach to Linear Regression", IEEE Signal Processing Magazine, Nov. 2008, pp. 159-163.
"Chemistry of Aqueous Chlorine", White's Handbook of Chlorination and Alternative Disinfectants, 2010, pp. 102-117, 5th Edition.
Demir, et al., Feedback control over the chlorine disinfection process at a wastewater treatment plant using a Smith predictor, a method of characteristics and odometric transformation, J Env Chem Engg, 2 (2014) 1088-1097 (Year: 2014).

* cited by examiner

CHEMICAL CONTROL SYSTEMS AND METHODS FOR CONTROLLING DISINFECTANTS

The subject application claims the benefit of provisional application Ser. No. 62/560,252 filed Sep. 19, 2017, which is incorporated herein by reference.

BACKGROUND OF THE INVENTION

Field of the Invention

The present invention relates to chemical control systems for controlling disinfectants, such as chloramines, and methods of operating such systems.

Description of Related Art

Water utilities typically add disinfectants to water systems to prevent contamination from germs and bacteria. The most commonly used secondary disinfectant is chlorine; however, while chlorine is a strong disinfectant, it has a short residual life and readily forms disinfection byproducts such as trihalomethanes. In order to avoid the drawbacks associated with chlorine, many water utilities are turning to chloramines as an alternative. As compared to chlorine, chloramines have a longer residual life and are less prone to disinfection byproduct formation. Despite these advantages, chloramine usage can be problematic. For instance, a water system is typically dosed with hypochlorite and ammonia to produce monochloramine; however, if the chlorine-to-ammonia ratio is not accurately controlled, undesirable side-effects occur such as nitrification, over-chlorination, and low oxidation levels. Thus, it is desirable to provide a chemical injection system that can be accurately controlled to continuously produce stable forms of monochloramine in a water system at a desired concentration.

SUMMARY OF THE INVENTION

Generally, provided is an improved chloramine injection and control system and method.

In one preferred and non-limiting embodiment or aspect, provided is a method of automatically controlling chloramine concentration in a body of water contained in a reservoir. The method includes: (a) determining residual chloramine concentration in a water sample obtained from the body of water; (b) determining at least one of the following when the residual chloramine concentration is below a predetermined target chloramine concentration level: (i) an average rate of change in total chlorine concentration based on residual total chlorine concentrations of water samples obtained from the body of water; and (ii) an average rate of change in oxidation-reduction potential based on oxidation-reduction potentials of water samples obtained from the body of water; and (c) automatically engaging a supply of ammonia and a supply of chlorine to add both ammonia and chlorine to the body of water at a weight ratio of chlorine to ammonia of 5:1 or less when: (i) the average rate of change in total chlorine concentration is below a set rate of change in total chlorine concentration; (ii) the average rate of change in oxidation-reduction potential is above a set rate of change in oxidation-reduction potential; or (iii) the average rate of change in total chlorine concentration is below a set rate of change in total chlorine concentration and the average rate of change in oxidation-reduction potential is above a set rate of change in oxidation-reduction potential.

In some preferred and non-limiting embodiments or aspects, the average rate of change in total chlorine concentration is determined in step (b), and ammonia and chlorine are both added to the body of water at a weight ratio of chlorine to ammonia of 5:1 or less in step (c) when (i) the average rate of change in total chlorine concentration is below the set rate of change in total chlorine concentration. In another preferred and non-limiting embodiment or aspect, the average rate of change in oxidation-reduction potential is determined in step (b), and ammonia and chlorine are both added to the body of water at a weight ratio of chlorine to ammonia of 5:1 or less in step (c) when (ii) the average rate of change in oxidation-reduction potential is above the set rate of change in oxidation-reduction potential. In yet another preferred and non-limiting embodiment or aspect, the average rate of change in total chlorine concentration and the average rate of change in oxidation-reduction potential is determined in step (b), and ammonia and chlorine are both added to the body of water at a weight ratio of chlorine to ammonia of 5:1 or less in step (c) when (iii) the average rate of change in total chlorine concentration is below the set rate of change in total chlorine concentration and the average rate of change in oxidation-reduction potential is above the set rate of change in oxidation-reduction potential.

In some preferred and non-limiting embodiments or aspects, the method further includes automatically engaging a supply of chlorine to add chlorine only to the body of water if the residual chloramine concentration in the water sample obtained from the body of water in step a) is below the predetermined target chloramine concentration level. In another preferred and non-limiting embodiment or aspect, the method further includes automatically engaging a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

In certain preferred and non-limiting embodiments or aspects, a feed rate of the chlorine and ammonia supplied to the body of water after step a) is different than a feed rate of the chlorine and ammonia supplied to the body of water in step c).

In some preferred and non-limiting embodiments or aspects, the average rate of change in total chlorine concentration and the average rate of change in oxidation-reduction potential in step (b) is determined when the supply of chlorine is disengaged. Further, the average rate of change in total chlorine concentration is determined by measuring the change in residual total chlorine concentration in consecutively obtained water samples over a fixed period of time, and the average rate of change in oxidation-reduction potential is determined by measuring the change in oxidation-reduction potential in consecutively obtained water samples over a fixed period of time.

In some preferred and non-limiting embodiments or aspects, if the average rate of change in total chlorine concentration is determined to be at or above the set rate of change in total chlorine concentration, chlorine only is added to the body of water. Further, in another preferred and non-limiting embodiment or aspect, if the average rate of change in oxidation-reduction potential is determined to be at or below the set rate of change in oxidation-reduction potential, chlorine only is added to the body of water.

Moreover, the supply of chlorine and the supply of ammonia are added to the body of water during step (c) until a subsequently obtained water sample is determined to be at or above the predetermined target chloramine concentration level.

In some preferred and non-limiting embodiments or aspects, the predetermined target chloramine concentration level comprises a minimum predetermined total chlorine concentration set-point and a maximum predetermined total chlorine concentration set-point. Further, the feed rate of the chlorine and/or the ammonia is decreased when the total chlorine concentration is at or above the minimum predetermined total chlorine concentration set-point and below the maximum predetermined total chlorine concentration set-point. In addition, the supply of chlorine and the supply of ammonia are disengaged when the total chlorine concentration is at or above the maximum predetermined total chlorine concentration set-point.

In certain preferred and non-limiting embodiments or aspects, the feed rate of the chlorine and ammonia are determined by reservoir water volume and dwell time. Further, the residual chloramine concentration can be based on a residual total chlorine concentration and the predetermined target chloramine concentration level can be based on a target total chlorine concentration level. The oxidation-reduction potentials of the samples can be determined by measuring millivolts of the water samples.

The present invention is also directed to a treatment delivery system for automatically controlling chloramine concentration in a body of water contained in a reservoir. The system includes: a chemical dosing assembly; a water sampling assembly configured to extract water sample from the body of water at different points in time; one or more analyzers in fluid communication with the water sampling assembly and configured to determine at least residual total chlorine concentration and optionally oxidation-reduction potential in the water samples; a controller in operable communication with the analyzers; and one or more computer-readable storage mediums in operable communication with the controller and containing programming instructions that, when executed, cause the controller to: (a) determine residual chloramine concentration in a water sample obtained from the body of water; (b) determine at least one of the following when the residual chloramine concentration is below a predetermined target chloramine concentration level: (i) an average rate of change in total chlorine concentration based on residual total chlorine concentrations of water samples obtained from the body of water; and (ii) an average rate of change in oxidation-reduction potential based on oxidation-reduction potentials of water samples obtained from the body of water; and (c) automatically engage a supply of ammonia and a supply of chlorine to add both ammonia and chlorine to the body of water at a weight ratio of chlorine to ammonia of 5:1 or less when: (i) the average rate of change in total chlorine concentration is below a set rate of change in total chlorine concentration while chlorine is added to the body of water; (ii) the average rate of change in oxidation-reduction potential is above a set rate of change in oxidation-reduction potential while chlorine is added to the body of water; or (iii) the average rate of change in total chlorine concentration is below a set rate of change in total chlorine concentration and the average rate of change in oxidation-reduction potential is above a set rate of change in oxidation-reduction potential.

In some preferred and non-limiting embodiments or aspects, the chemical dosing assembly is at least partially submerged in the body of water. Further, in certain preferred and non-limiting embodiments or aspects, the computer-readable storage mediums in operable communication with the controller further comprise programming instructions that, when executed, cause the controller to automatically engage a supply of chlorine to add chlorine only to the body of water if the residual chloramine concentration in the water sample obtained from the body of water in step a) is below the predetermined target chloramine concentration level. In another preferred and non-limiting embodiment or aspect, the computer-readable storage mediums in operable communication with the controller further comprise programming instructions that, when executed, cause the controller to automatically engage a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

Additional preferred and non-limiting embodiments or aspects are set forth and described in the following clauses.

Clause 1: A method of automatically controlling chloramine concentration in a body of water contained in a reservoir, the method comprising: a) determining residual chloramine concentration in a water sample obtained from the body of water; b) determining at least one of the following when the residual chloramine concentration is below a predetermined target chloramine concentration level: i) an average rate of change in total chlorine concentration based on total chlorine concentrations of water samples obtained from the body of water; and ii) an average rate of change in oxidation-reduction potential based on oxidation-reduction potentials of water samples obtained from the body of water; and c) automatically engaging a supply of ammonia and a supply of chlorine to add both ammonia and chlorine to the body of water at a weight ratio of chlorine to ammonia of 5:1 or less when: i) the average rate of change in total chlorine concentration is below a set rate of change in total chlorine concentration; ii) the average rate of change in oxidation-reduction potential is above a set rate of change in oxidation-reduction potential; or iii) the average rate of change in total chlorine concentration is below a set rate of change in total chlorine concentration and the average rate of change in oxidation-reduction potential is above a set rate of change in oxidation-reduction potential.

Clause 2: The method of clause 1, wherein the average rate of change in total chlorine concentration is determined in step b), and wherein ammonia and chlorine are both added to the body of water at a weight ratio of chlorine to ammonia of 5:1 or less in step c) when i) the average rate of change in total chlorine concentration is below the set rate of change in total chlorine concentration.

Clause 3: The method of clause 1, wherein the average rate of change in oxidation-reduction potential is determined in step b), and wherein ammonia and chlorine are both added to the body of water at a weight ratio of chlorine to ammonia of 5:1 or less in step c) when ii) the average rate of change in oxidation-reduction potential is above the set rate of change in oxidation-reduction potential.

Clause 4: The method of any of clause 1, wherein the average rate of change in total chlorine concentration and the average rate of change in oxidation-reduction potential is determined in step b), and wherein ammonia and chlorine are both added to the body of water at a weight ratio of chlorine to ammonia of 5:1 or less in step c) when iii) the average rate of change in total chlorine concentration is below the set rate of change in total chlorine concentration and the average rate of change in oxidation-reduction potential is above the set rate of change in oxidation-reduction potential.

Clause 5: The method of any of clauses 1 to 4, further comprising automatically engaging a supply of chlorine to add chlorine only to the body of water if the residual chloramine concentration in the water sample obtained from the body of water in step a) is below the predetermined target chloramine concentration level.

Clause 6: The method of any of clauses 1 to 4, further comprising automatically engaging a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

Clause 7: The method of clause 6, wherein a feed rate of the chlorine and ammonia supplied to the body of water after step a) is different than a feed rate of the chlorine and ammonia supplied to the body of water in step c).

Clause 8: The method of clause 1 or 4, wherein the average rate of change in total chlorine concentration and the average rate of change in oxidation-reduction potential in step b) is determined when the supply of chlorine and ammonia are disengaged.

Clause 9: The method of any of clauses 1 to 8, wherein the average rate of change in total chlorine concentration is determined by measuring the change in residual total chlorine concentration in consecutively obtained water samples over a fixed period of time, and wherein the average rate of change in oxidation-reduction potential is determined by measuring the change in oxidation-reduction potential in consecutively obtained water samples over a fixed period of time.

Clause 10: The method of any of clauses 1 to 9, wherein, if the average rate of change in total chlorine concentration is determined to be at or above the set rate of change in total chlorine concentration, chlorine only is added to the body of water or chlorine and ammonia are added to the body of water at a weight ratio of chlorine to ammonia of greater than 5:1.

Clause 11: The method of any of clauses 1 to 9, wherein, if the average rate of change in oxidation-reduction potential is determined to be at or below the set rate of change in oxidation-reduction potential, chlorine only is added to the body of water or chlorine and ammonia are added to the body of water at a weight ratio of chlorine to ammonia of greater than 5:1.

Clause 12: The method of any of clauses 1 to 11, wherein the supply of chlorine and the supply of ammonia are added to the body of water during step c) until a subsequently obtained water sample is determined to be at or above the predetermined target chloramine concentration level.

Clause 13: The method of any of clauses 1 to 12, wherein the predetermined target chloramine concentration level comprises a minimum predetermined total chlorine concentration set-point and a maximum predetermined total chlorine concentration set-point, and wherein the feed rate of the chlorine and/or the ammonia is decreased when the total chlorine concentration is at or above the minimum predetermined total chlorine concentration set-point and below the maximum predetermined total chlorine concentration set-point, and wherein the supply of chlorine and the supply of ammonia are disengaged when the total chlorine concentration is at or above the maximum predetermined total chlorine concentration set-point.

Clause 14: The method of any of clauses 1 to 13, wherein the feed rate of the chlorine and ammonia are determined by reservoir water volume and dwell time.

Clause 15: The method of any of clauses 1 to 14, wherein the residual chloramine concentration is based on a residual total chlorine concentration and the predetermined target chloramine concentration level is based on a target total chlorine concentration level.

Clause 16: The method of any of clauses 1 to 15, wherein the oxidation-reduction potentials of the samples are determined by measuring millivolts of the water samples.

Clause 17: A treatment delivery system for automatically controlling chloramine concentration in a body of water contained in a reservoir comprising: a chemical dosing assembly; a water sampling assembly configured to extract a water sample from the body of water at different points in time; one or more analyzers in fluid communication with the water sampling assembly and configured to determine at least total chlorine concentration, and optionally, oxidation-reduction potential in the water samples; a controller in operable communication with the one or more analyzers; and one or more computer-readable storage mediums in operable communication with the controller and containing programming instructions that, when executed, cause the controller to: a) determine residual chloramine concentration in a water sample obtained from the body of water; b) determine at least one of the following when the residual chloramine concentration is below a predetermined target chloramine concentration level: i) an average rate of change in total chlorine concentration based on residual total chlorine concentrations of water samples obtained from the body of water; and ii) an average rate of change in oxidation-reduction potential based on oxidation-reduction potentials of water samples obtained from the body of water; and c) automatically engage a supply of ammonia and a supply of chlorine to add both ammonia and chlorine to the body of water at a weight ratio of chlorine to ammonia of 5:1 or less when: i) the average rate of change in total chlorine concentration is below a set rate of change in total chlorine concentration while chlorine is added to the body of water; ii) the average rate of change in oxidation-reduction potential is above a set rate of change in oxidation-reduction potential while chlorine is added to the body of water; or iii) the average rate of change in total chlorine concentration is below a set rate of change in total chlorine concentration and the average rate of change in oxidation-reduction potential is above a set rate of change in oxidation-reduction potential.

Clause 18: The system of clause 17, wherein the chemical dosing assembly is at least partially submerged in the body of water.

Clause 19: The system of any clauses 17 or 18, wherein the computer-readable storage mediums in operable communication with the controller further comprise programming instructions that, when executed, cause the controller to automatically engage a supply of chlorine to add chlorine only to the body of water if the residual chloramine concentration in the water sample obtained from the body of water in step a) is below the predetermined target chloramine concentration level.

Clause 20: The system of clauses 17 or 18, wherein the computer-readable storage mediums in operable communication with the controller further comprise programming instructions that, when executed, cause the controller to automatically engage a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

DETAILED DESCRIPTION OF THE INVENTION

Figure 1:
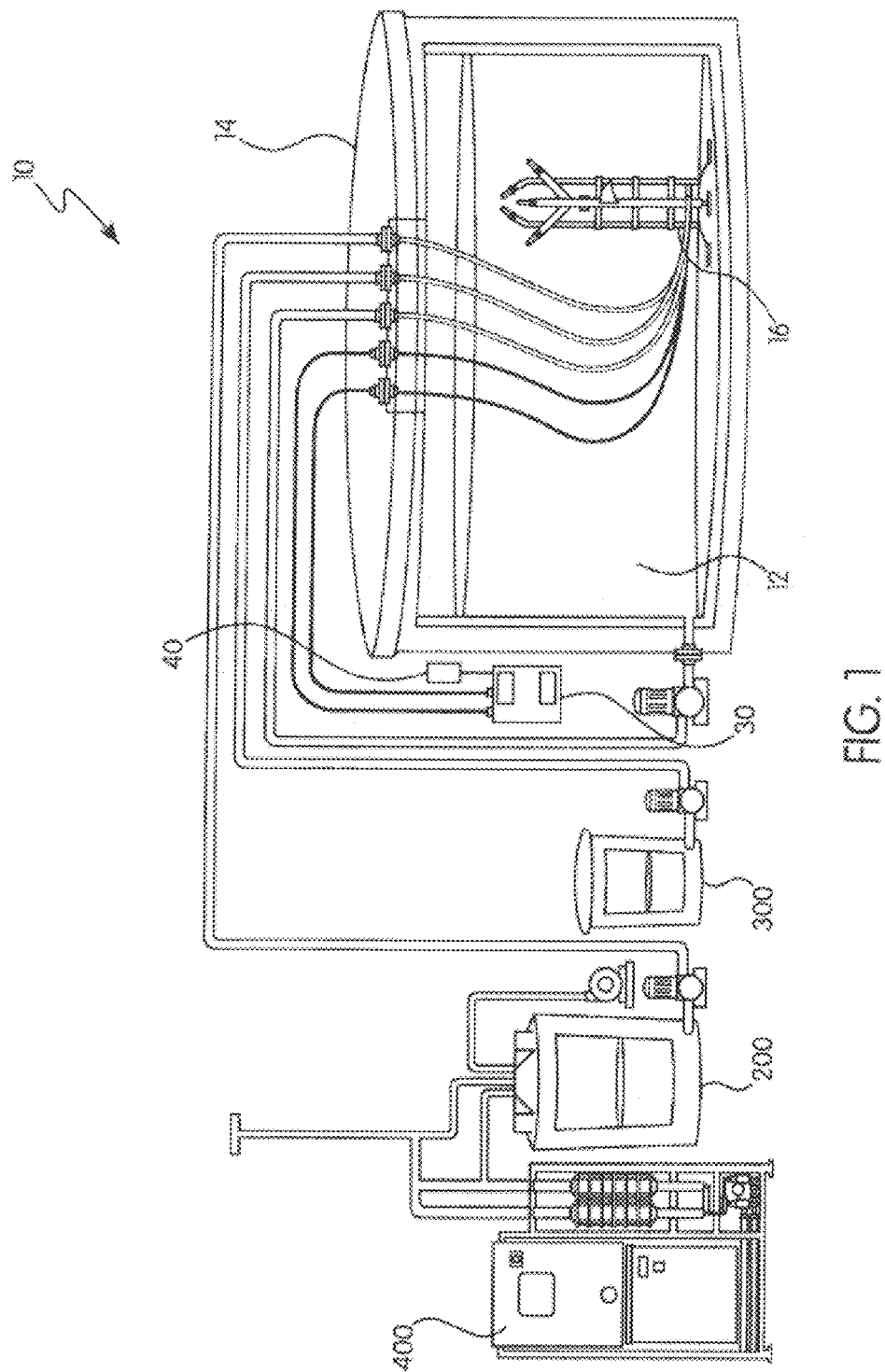
FIG. 1 illustrates a treatment delivery system according to the principles of the present invention.

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Further, the terms "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the specification, are simply exemplary embodiments of the invention. Hence, specific dimensions and other physical characteristics related to the embodiments disclosed herein are not to be considered as limiting.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

Referring to FIG. 1, and in one preferred and non-limiting embodiment or aspect, the present invention is directed to a treatment delivery system 10 that can be used to automatically control chloramine concentration in a body of water 12 contained in a reservoir 14. The term "automatic control" refers to the absence of substantial participation of a human operator in normal operations manually controlling the controllable components. As such, the treatment delivery system 10 can be controlled without an operator monitoring or adjusting the various parameters of the treatment delivery system 10 during normal operations.

Figure 2:
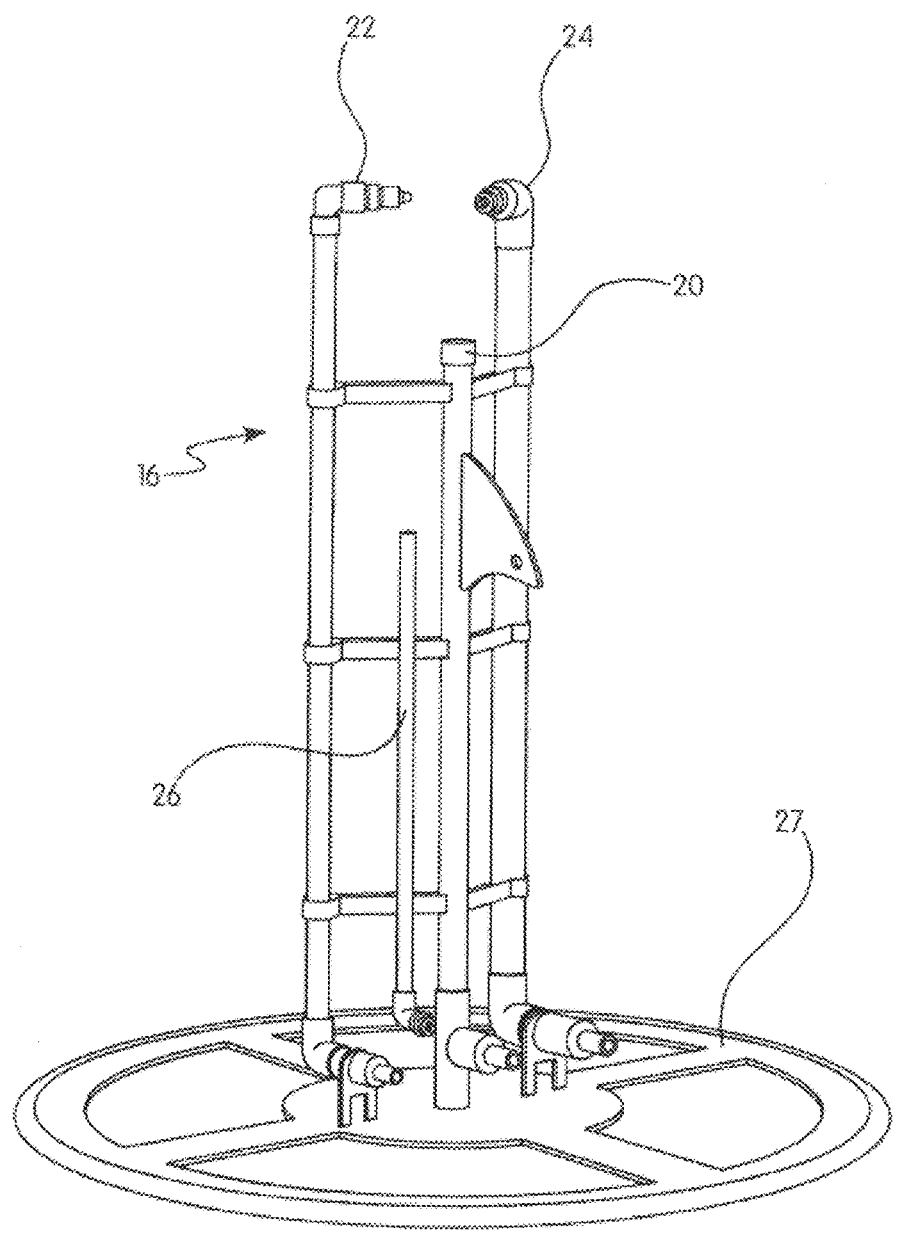
FIG. 2 illustrates a chemical dosing assembly according to the principles of the present invention.

As shown in FIG. 1, the treatment delivery system 10 can include a chemical dosing assembly 16 that can be at least partially submerged in the body of water 12. Referring to FIG. 2, and in one preferred and non-limiting embodiment or aspect, the chemical dosing assembly 16 can include a water motive tube 20, a first chemical treatment flow tube 22, and optionally, a second chemical treatment flow tube 24. The water motive tube 20 and chemical treatment flow tubes 22, 24 of the chemical dosing assembly 16 can be oriented to expel water and chemicals, respectively, into the body of water 12 held in the reservoir 14. The chemicals used with the chemical treatment tubes 22, 24 can be selected to form chloramine, such as monochloramine, when expelled into a jet of water expelled from the water motive tube 20. For example, the first chemical treatment flow tube 22 can be in fluid communication with a source of chlorine and can be configured to expel chlorine into the body of water 12 while the second chemical treatment flow tube 24 can be in fluid communication with a source of ammonia and can be configured to expel ammonia into the body of water 12. Because of the configuration of the nozzle ends of the first and second chemical treatment flow tubes 22, 24, the chemicals expelled through the ends thereof come into almost immediate contact with one another and can begin reacting soon after being expelled into the body of water 12.

In addition, and in one preferred and non-limiting embodiment or aspect, the water motive tube 20 is positioned below the release point of the first and second chemical treatment flow tubes 22, 24 to circulate the chemicals into the body of water 12. The flow of water out of the water motive tube 20 can also create a high energy, high velocity mixing zone directly above the water motive tube 20 where the chemicals can be released, which helps the chemicals interact and form a particular compound, such as monochloramine. The treatment delivery system 10 can include multiple chemical dosing assemblies 16 strategically located throughout the reservoir 14.

The treatment delivery system 10 can further include a water sampling assembly 26 that is configured to obtain or extract water samples from the body of water 12 at different points in time, such as continuously, periodically, and/or according to a pre-programmed cycle. As shown in FIG. 2, the water sampling line 26 can be a component of the chemical dosing assembly 16. For example, the water motive tube 20, chemical treatment tubes 22, 24, and water sampling assembly 26 of the chemical dosing assembly 16 can be secured to a frame 27 that is adapted to rest at the bottom of the reservoir 14. Alternatively, the water motive tube 20, the chemical treatment tubes 22, 24, and the water sampling assembly 26 can extend into the reservoir 14 to a desired depth. Yet another alternative (not shown) is that the water sampling assembly 26 can be separate from the chemical dosing assembly 16 and may be located at any location within the reservoir 14. Treatment delivery system 10 may also include multiple water sampling assemblies 26 positioned throughout the reservoir 14. It is appreciated that the water sample can also be obtained from other methods including, but not limited to, water sampling with a submersible pump positioned inside the reservoir 14.

Referring to FIG. 1, and in one preferred and non-limiting embodiment or aspect, the treatment delivery system 10 can also include one or more analyzers 30 that are in fluid communication with the water sampling assembly 26. The analyzer(s) 30 are configured to receive the water samples and analyze the contents thereof in order to determine the chloramine concentration. Various methods are known to determine the chloramine concentration in a sample of water. In one preferred and non-limiting embodiment or aspect, the analyzer(s) 30 are programmed or configured to determine the concentration of total chlorine of the water sample, the oxidation-reduction potential of the water sample, or both the concentration of total chlorine and the oxidation-reduction potential of the water sample. The present invention can also include analyzer(s) 30 programmed to determine other parameters including, but not limited to, pH, temperature, and combinations thereof. It will be appreciated that the analyzer(s) 30 may be a standalone device or, in other embodiments, may be software and/or firmware executed by the controller 40 or other processor.

In one preferred and non-limiting embodiment or aspect, the analyzer 30 is, or includes, a total chlorine analyzer, such as the total chlorine analyzer commercially available from ProMinent Fluid Controls, Inc. of Pittsburgh, Pa., which can be used to indirectly measure the chloramine concentration. The analyzer(s) 30 can also be configured to measure oxidation-reduction potential which reflects the ability of certain chemical components in the water to accept or lose electrons. It is appreciated that the total chlorine residual and/or oxidation-reduction potential measurements in a water sample are used to determine the residual chloramine concentration either by the analyzer 30 or by a controller 40 or other processor associated therewith. In some preferred and non-limiting embodiment or aspect, the analyzer(s) 30 is, or also includes, a chloramine analyzer, such as the APA 6000 Ammonia and Monochloramine Analyzer commercially available from Hach Company of Loveland, Colo., which can directly measure the chloramine concentration in the water sample.

As indicated, the treatment delivery system 10 can further include a controller 40 that is in operable communication with the analyzer(s) 30 so that measurements and other data gathered, and/or determined by the analyzer(s) 30, can be transferred or accessed by the controller 40. One or more computer-readable storage mediums can be in operable communication with the controller 40. The computer-readable storage mediums can contain programming instructions that, when executed, cause the controller 40 to perform multiple tasks. This includes programming algorithms such as those described herein that allow the controller 40 to control the administration of chlorine and/or ammonia into the body of water 12 for establishing, reestablishing, and maintaining target residual chloramine levels within the body of water 12. The programming instructions can be updated and modified. For example, the target residual chloramine level can be changed as can the flow rates of the chlorine and/or ammonia and the water sampling frequency.

In one example, and in one preferred and non-limiting embodiment or aspect, the programming instructions, when executed, can cause the controller 40 to: measure and/or analyze a water sample obtained from the body of water 12, and/or determine whether the residual chloramine concentration in the water sample is below a predetermined residual chloramine concentration set-point or below a chloramine concentration percentage of a predetermined residual chloramine concentration set-point (both which are also referred to herein as a "predetermined chloramine concentration target level"); when the residual chloramine concentration is below a predetermined target chloramine concentration level, determine an average rate of change in total chlorine concentration based on residual total chlorine concentrations of water samples obtained from the body of water and/or an average rate of change in oxidation-reduction potential based on oxidation-reduction potentials of water samples obtained from the body of water; and automatically engage a supply of ammonia and a supply of chlorine to add both ammonia and chlorine to the body of water at a weight ratio of chlorine to ammonia of 5:1 or less when: the average rate of change in total chlorine concentration is below a set rate of change in total chlorine concentration; the average rate of change in oxidation-reduction potential is above a set rate of change in oxidation-reduction potential; or the average rate of change in total chlorine concentration is below a set rate of change in total chlorine concentration and the average rate of change in oxidation-reduction potential is above a set rate of change in oxidation-reduction potential. It is appreciated that controller 40 may include one or more microprocessors, CPUs, and/or other computing devices.

As further shown in FIG. 1, and in one preferred and non-limiting embodiment or aspect, treatment delivery system 10 can include multiple chemical storage tanks, such as a first chemical storage tank 200 and a second chemical storage tank 300, which are configured to transport chemicals to the chemical dosing assembly 16 via one or more metering pumps. As indicated, the treatment delivery system 10 can deliver a source of chlorine and a source of ammonia into the body of water 12. As such, the chemical storage tanks 200, 300 can store a source of chlorine and a source of ammonia. Because the treatment delivery system 10 is capable of delivering any type of chlorine and ammonia source, the chemical storage tanks 200, 300 can be selected to store various sources of chlorine and ammonia. Non-limiting examples of chlorine sources that can be used with the present invention include pressurized chlorine gas and hypochlorites such as sodium hypochlorite, potassium hypochlorite, and calcium hypochlorite. Non-limiting examples of ammonia sources that can be used with the present invention include pressurized anhydrous ammonia, aqueous ammonia, and liquid ammonium sulfate. The chemical storage tanks 200, 300 can also be supplied by on-site chemical generation systems, such as an on-site hypochlorite generation system 400 as shown in FIG. 1 for example that can generate hypochlorite based chemicals (e.g., sodium hypochlorite or potassium hypochlorite) directly at the water treatment site.

Non-limiting examples of chemical dosing assemblies, chemical generation systems, and the like are disclosed in U.S. Pat. No. 9,039,902, which is incorporated by reference herein in its entirety. In particular, U.S. Pat. No. 9,039,902 describes chemical dosing assemblies, as well as a hypochlorite generation system, that can be used as the source of chlorine that is present in first chemical storage tank 200 and, ultimately, supplied to the body of water 12. The treatment delivery system 10 can also utilize other mixing systems as well. For example, the treatment delivery system 10 can also utilize the mixing system disclosed in U.S. Pat. No. 7,862,302, which is incorporated by reference herein in its entirety.

As indicated, the present invention is also directed to a method of automatically controlling chloramine concentration in a body of water 12 contained in a reservoir 14. The method can be implemented through one or more algorithms and controls contained in programming instructions that, when executed, cause the system 10 to take certain actions, as described below.

The method can first include measuring, analyzing, and/or determining the residual chloramine concentration in a water sample obtained from the body of water 12. The water sample can be obtained with the water sampling assembly 26 and transported to the analyzer 30 that is in fluid communication with the water sampling assembly 26. The analyzer 30 can then measure, analyze, and/or determine the residual chloramine concentration. The determination of the residual chloramine concentration can include measuring the residual total chlorine concentration in the water sample.

The residual chloramine concentration determination can be reported to a controller 40 that is in operable communication with one or more computer-readable storage mediums. The controller 40 also has knowledge of, or access to, information about the predetermined chloramine concentration target level, which can be based on a residual total chlorine concentration target level, for example. In some preferred and non-limiting embodiments or aspects, if the residual chloramine concentration in the water sample is determined to be below the predetermined chloramine concentration target level (which can be based on a residual total chlorine concentration set-point, for example), additional water samples are obtained from the body of water 12 to determine the average rate of change in total chlorine concentration based on residual total chlorine concentrations of the water samples and/or an average rate of change in oxidation-reduction potential based on oxidation-reduction potentials of the water samples.

As used herein, the "average rate of change in the total chlorine concentration" refers to the change in the total chlorine concentration value over time based on the total chlorine concentration in two or more water samples. Further, the "average rate of change in the oxidation-reduction potential" refers to the change in the oxidation-reduction potential value over time based on the oxidation-reduction potential in two or more water samples.

In some preferred and non-limiting embodiments or aspects, the average rate of change in total chlorine concentration and/or oxidation-reduction potential is determined by comparing the total chlorine concentration and/or oxidation-reduction potential in a plurality of water samples obtained after a fixed period of time. For example, the average rate of change in total chlorine concentration and/or oxidation-reduction potential can be based on the average change in total chlorine concentration and/or oxidation-reduction potential between consecutively obtained water samples over a specified period of time, such as 10 minutes or 30 minutes or one hour for example.

The rate of change in the total chlorine concentration or oxidation-reduction potential is determined by the least squares regression. Non-limiting examples of such equations are described in *Slope Filtering: An FIR Approach to Linear Regression*, IEEE SIGNAL PROCESSING MAGAZINE, November 2008, pages 159 to 163. The rate of change in the total chlorine concentration or oxidation-reduction potential can also be determined by the following formula: average rate of change=last determined total chlorine concentration value or oxidation-reduction potential value−first determined total chlorine concentration value or oxidation-reduction potential value/time the water sample of the last determined value was obtained−time the water sample of the first determined value was obtained. Thus, the programming instructions can include the average rate of change formula to allow the controller 40 to determine the average rate of change in total chlorine concentration and/or oxidation-reduction potential in the body of water 12.

After determining the average rate of change in total chlorine concentration and/or oxidation-reduction potential, ammonia and chlorine are both added to the body of water 12 at a weight ratio of chlorine to ammonia of 5:1 or less if: the average rate of change in total chlorine concentration is below a set rate of change in chloramine concentration; the average rate of change in oxidation-reduction potential is above a set rate of change in oxidation-reduction potential; or the average rate of change in total chlorine concentration is below a set rate of change in total chlorine concentration and the average rate of change in oxidation-reduction potential is above a set rate of change in oxidation-reduction potential when the supply of chlorine is disengaged or while chlorine is added to the body of water 12. The chlorine and ammonia can be added to the body of water 12 as previously described through treatment tubes 22 and 24 of the chemical dosing assembly 16.

As used herein, a "set rate of change in total chlorine concentration" refers to a predetermined (target) increase or decrease in the rate of change in total chlorine concentration, and a "set rate of change in oxidation-reduction potential" refers to a predetermined (target) increase or decrease in the rate of change in oxidation-reduction potential. For example, the set rate of change in total chlorine concentration can be 0.05 mg/L/hour and if the average rate of change in residual total chlorine concentration is determined to be below 0.05 mg/L/hour, the programming instructions will cause the controller 40 to automatically engage (or control) a supply of chlorine and ammonia to add both ammonia and chlorine to the body of water 12 at a weight ratio of chlorine to ammonia of 5:1 or less. In another non-limiting example, the method of the present invention includes a set rate of change in oxidation-reduction potential such as 40 mV/hour and if the average rate of change in oxidation-reduction potential is determined to be above 40 mV/hour, the programming instructions will cause the controller 40 to automatically engage (or control) a supply of chlorine and ammonia to add both ammonia and chlorine to the body of water 12 at a weight ratio of chlorine to ammonia of 5:1 or less.

In yet another non-limiting example, the method of the present invention includes a set rate of change in total chlorine concentration such as 0.05 mg/L/hour and a set rate of change in oxidation-reduction potential such as 40 mV/hour. If the average rate of change in residual total chlorine concentration is determined to be below 0.05 mg/L/hour determined and the average rate of change in oxidation-reduction potential is determined to be above 40 mV/hour, the programming instructions will cause the controller 40 to automatically engage (or control) a supply of chlorine and ammonia to add both ammonia and chlorine to the body of water 12 at a weight ratio of chlorine to ammonia of 5:1 or less.

It is appreciated that the set rate of change in total chlorine concentration and/or oxidation-reduction potential can be based on a positive or negative rate of change. For instance, the set rate of change in total chlorine concentration can be a positive rate of change and the set rate of change in oxidation-reduction potential can be a negative rate of change. As used herein, a "positive rate of change" refers to an increase in the total chlorine concentration and/or oxidation-reduction potential over a period of time, and a "negative rate of change" refers to a decrease in the total chlorine concentration and/or oxidation-reduction potential over a period of time.

In some preferred and non-limiting embodiments or aspects, the method step of adding both chlorine and ammonia into the body of water 12 at a weight ratio of chlorine to ammonia of 5:1 or less is controlled by one of the following algorithms: (1) $w<y$=add both chlorine and ammonia at a weight ratio of chlorine to ammonia of 5:1 or less, where "w" is the rate of change in total chlorine concentration determined from the water samples and "y" is the set rate of change in total chlorine concentration; (2) $o>p$=add both chlorine and ammonia at a weight ratio of chlorine to ammonia of 5:1 or less, where "o" is the rate of change in oxidation-reduction potential determined from the water samples and "p" is the set rate of change in oxidation-reduction potential; and/or (3) $w<y$ and $o>p$=add both chlorine and ammonia at a weight ratio of chlorine to ammonia of 5:1 or less, where "w" is the rate of change in total chlorine concentration determined from the water samples, "y" is the set rate of change in total chlorine concentration, "o" is the rate of change in oxidation-reduction potential determined from the water samples, and "p" is the set rate of change in oxidation-reduction potential. Thus, the programming instructions can include at least one, or all, of the previous algorithms that, when satisfied, will cause the controller 40 to automatically engage (or control) a supply of chlorine and a supply of ammonia to add both chlorine and ammonia to the body of water 12 at a weight ratio of chlorine to ammonia of 5:1 or less.

Chlorine and ammonia are added to the body of water 12 until a subsequently obtained water sample is determined to be at or above the predetermined chloramine concentration target level, at which point the programming instructions will cause the controller 40 to stop the supply of chlorine and the supply of ammonia into the body of water 12.

In some preferred and non-limiting embodiments or aspects, the previously described method step of stopping the addition of chlorine and ammonia into the body of water 12 is controlled by the following algorithm in which the predetermined chloramine concentration target level is a residual chloramine concentration set-point based on a single value: $z \geq x$=stop the supply of chlorine and ammonia, where "z" is the residual chloramine concentration determined in a subsequent water sample as chlorine and ammonia are being supplied to the body of water 12, and "x" is a residual chloramine concentration set-point. Thus, the programming instructions can include algorithm that, when satisfied, will cause the controller 40 to stop automatically engaging (or controlling) a supply of chlorine and a supply of ammonia, and therefore, stop adding chlorine and ammonia to the body of water 12.

In some preferred and non-limiting embodiments or aspects, the controller 40 is programmed to stop the supply of chlorine and ammonia into the body of water 12 when the residual chloramine concentration is above a particular percentage of the residual chloramine concentration set-point. For example, the controller 40 can be programmed to stop the supply of chlorine and ammonia into the body of water 12 when the residual chloramine concentration in a water sample is a percentage selected within a range of 101% to 110% of the residual chloramine concentration set-point, or a percentage selected within a range of 101% to 105% of the residual chloramine concentration set-point.

In such preferred and non-limiting embodiments or aspects, different programming algorithms are used to control when the supply of chlorine and ammonia into the body of water 12 are stopped. For instance, the method step of stopping the supply of chlorine can be controlled by the following algorithm: $z>[(t)(x)]$=stop the supply of chlorine and ammonia, where "z" is the residual chloramine concentration determined in a subsequent water sample as chlorine and ammonia are being supplied to the body of water 12, "t" is a percentage selected within a range of 101% to 110%, and "x" is the residual chloramine concentration set-point. Thus, the programming instructions can include, or can be modified to include, the above algorithm that, when satisfied, will cause the controller 40 to stop automatically engaging (or controlling) a supply of chlorine and a supply of ammonia.

In some preferred and non-limiting embodiments or aspects, the predetermined chloramine concentration target level for controlling and stopping the supply of chlorine and ammonia can include a minimum predetermined chloramine concentration set-point and a maximum predetermined chloramine concentration set-point. The programming instructions will cause the controller 40 to perform certain functions when the chloramine concentration is at or above the minimum predetermined chloramine concentration set-point but below the maximum predetermined chloramine concentration set-point, and to perform different functions when the chloramine concentration is at or above the maximum predetermined chloramine concentration set-point. For instance, the predetermined chloramine concentration target level for controlling and stopping the supply of chlorine and ammonia can comprise: (i) a minimum predetermined chloramine concentration set-point that causes the controller 40 to decrease the feed rate of the chlorine and/or the ammonia into the body of water 12; and (ii) a maximum predetermined chloramine concentration set-point that causes the controller 40 to stop the supply of chlorine and/or the ammonia into the body of water 12.

In some preferred and non-limiting embodiments or aspects, the method step of controlling and stopping the addition of chlorine and ammonia into the body of water 12 is controlled by the following algorithms: $z \geq x$ and $z \leq y$=decrease the feed rate of the supply of chlorine and ammonia; and $z \geq y$=stop the supply of chlorine and ammonia, where "z" is the residual chloramine concentration determined in a subsequent water sample as chlorine and ammonia are being supplied to the body of water 12, "x" is a minimum predetermined chloramine concentration set-point, and "y" is a maximum predetermined chloramine concentration set-point. Thus, the programming instructions can include the above algorithms that, when satisfied, will cause the controller 40 to control and/or stop automatically engaging (or controlling) a supply of chlorine and a supply of ammonia, and therefore, modify and/or stop adding chlorine and ammonia to the body of water 12.

As previously mentioned, the predetermined chloramine concentration target level for controlling and stopping the supply of chlorine and ammonia can be based on a total chlorine concentration target level. Thus, it is appreciated that the predetermined chloramine concentration target level used in the previously described method steps and algorithms for controlling and stopping the supply of chlorine and ammonia can be based on a predetermined total chlorine concentration set-point, a percentage of the predetermined total chlorine concentration set-point, or a minimum predetermined total chlorine concentration set-point and a maximum predetermined total chlorine concentration set-point. In such embodiments, the residual chloramine concentration is based on and/or determined from the residual total chlorine concentration in the water samples.

As indicated, the supply of chlorine can be engaged and added to the body of water 12 prior to determining the rate of change in total chlorine concentration and/or oxidation-reduction potential. For instance, in some preferred and non-limiting embodiments or aspects, chlorine, and optionally, ammonia are supplied to the body of water 12 after determining that the residual chloramine concentration in the water sample is below the predetermined chloramine concentration target level and before determining the average rate of change in total chlorine concentration and/or oxidation-reduction potential. In some preferred and non-limiting embodiments or aspects, the previously described method step of adding chlorine into the body of water 12 before determining the rate of change in total chlorine concentration and/or oxidation-reduction potential is controlled by the following algorithm: $z<x=$add chlorine, where "z" is the residual chloramine concentration determined in the water sample and "x" is the residual chloramine concentration set-point. Thus, the programming instructions can include the above algorithm that, when satisfied, will cause the controller 40 to automatically engage (or control) a supply of chlorine to add chlorine to the body of water 12.

As previously described, the chlorine and ammonia can both be supplied to the body of water 12 after determining that the residual chloramine concentration in the water sample is below the predetermined chloramine concentration target level and before determining the average rate of change in total chlorine concentration and/or oxidation-reduction potential. In such embodiments, the chlorine and ammonia are supplied to the body of water 12 at a weight ratio of chlorine to ammonia of greater than 5:1. In some preferred and non-limiting embodiments or aspects, the previously described method step of adding chlorine and ammonia into the body of water 12 before determining the rate of change in total chlorine concentration and/or oxidation-reduction potential is controlled by the following algorithm: $z<x=$add chlorine and ammonia at a weight ratio of chlorine to ammonia of greater than 5:1, where "z" is the residual chloramine concentration determined in the water sample and "x" is the residual chloramine concentration set-point. Thus, the programming instructions can include the above algorithm that, when satisfied, will cause the controller 40 to automatically engage (or control) a supply of chlorine and ammonia to add chlorine and ammonia to the body of water 12 at a weight ratio of chlorine to ammonia of greater than 5:1.

Further, in such embodiments where chlorine and ammonia are supplied to the body of water 12 at a weight ratio of chlorine to ammonia of greater than 5:1, the weight ratio of chlorine to ammonia is adjusted to 5:1 or less when the set rate of change in total chlorine concentration and/or the set rate of change in oxidation-reduction potential are not satisfied as previously described. Further, the feed rate of ammonia and chlorine supplied at a weight ratio of chlorine to ammonia of greater than 5:1 can be the same as or different than the feed rate of ammonia and chlorine supplied at a weight ratio of chlorine to ammonia of greater than 5:1. For example, the feed rate of ammonia and chlorine supplied at a weight ratio of chlorine to ammonia of greater than 5:1 can be the greater or lower than the feed rate of ammonia and chlorine supplied at a weight ratio of chlorine to ammonia of greater than 5:1.

In certain preferred and non-limiting embodiments or aspects, the method uses a chloramine concentration percentage to determine when to engage (or control) and add a supply of chlorine, and optionally, ammonia to the body of water 12 before determining the average rate of change in total chlorine concentration and/or oxidation-reduction potential. For instance, the programming instructions can cause the controller 40 to engage (or control) a supply of chlorine, and optionally, ammonia and add the chlorine, and optionally, ammonia to the body of water 12 when it is determined that the residual chloramine concentration in a water sample is below a percentage selected within a range of 99% to 80% of the residual chloramine concentration set-point, or below a percentage selected within a range of 99% to 85% of the residual chloramine concentration set-point, or below a percentage selected within a range of 99% to 90% of the residual chloramine concentration set-point, or below a percentage selected within a range of 99% to 95% of the residual chloramine concentration set-point.

In some preferred and non-limiting embodiments or aspects, the previously described method step of adding chlorine into the body of water 12 based on a chloramine concentration percentage is controlled by the following algorithm: $y<[(a)(x)]=$add chlorine, where "y" is the residual chloramine concentration determined in the first water sample, "a" is a percentage selected within a range of 99% to 80%, and "x" is the residual chloramine concentration set-point. Further, the previously described method step of adding chlorine and ammonia into the body of water 12 based on a chloramine concentration percentage is controlled by the following algorithm: $y<[(a)(x)]=$add chlorine and ammonia at a weight ratio of chlorine to ammonia of greater than 5:1, where "y" is the residual chloramine concentration determined in the first water sample, "a" is a percentage selected within a range of 99% to 80%, and "x" is the residual chloramine concentration set-point. Thus, the programming instructions can include, or can be modified to include, the above algorithm that, when satisfied, will cause the controller 40 to automatically engage (or control) a supply of chlorine to add chlorine to the body of water 12.

It is appreciated that the predetermined chloramine concentration target level used prior to determining the rate of change in total chlorine concentration and/or oxidation-reduction potential can be based on a total chlorine concentration target level. As such, the predetermined chloramine concentration target level used in the previously described method steps and algorithms and which is used before determining the rate of change in total chlorine concentration and/or oxidation-reduction potential can be based on a predetermined total chlorine concentration set-point or a percentage of the predetermined total chlorine concentration set-point. In such embodiments, the residual chloramine concentration is based on and/or determined from the residual total chlorine concentration in the water samples.

In some preferred and non-limiting embodiments or aspects, chlorine and ammonia are not added before determining the rate of change in total chlorine concentration and/or oxidation-reduction potential. In such embodiments, both chlorine and ammonia can be directly added after determining that the desired set rate of change in total chlorine concentration and the desired set rate of change oxidation-reduction potential are not achieved.

As previously described, both chlorine and ammonia are added to the body of water 12 if the residual chloramine concentration is below the predetermined chloramine concentration target level and the average rate of change in total chlorine concentration and/or oxidation-reduction potential is below or above the set rate of change in total chlorine concentration and/or oxidation-reduction potential such that the set rate of change in total chlorine concentration and/or oxidation-reduction potential is not achieved. Alternatively, if the residual chloramine concentration is below the predetermined chloramine concentration target level and the set rate of change in total chlorine concentration and/or oxidation-reduction potential is achieved, then chlorine and ammonia are not both added to the body of water 12.

In some preferred and non-limiting embodiments or aspects, when chlorine, and optionally, ammonia being supplied to the body of water 12 after determining that the residual chloramine concentration is below the predetermined chloramine concentration target level and the set rate of change in total chlorine concentration and/or oxidation-reduction potential is achieved, the controller 40 can continue to supply chlorine only to the body 12 or supply chlorine and ammonia at a weight ratio of chlorine to ammonia of greater than 5:1. The method step of continually adding chlorine when the set rate of change in total chlorine concentration and/or oxidation-reduction potential is achieved can be controlled by the following example algorithms: (i) w≥y and w'<x=add chlorine, where "w" is the rate of change in total chlorine concentration, "y" is the set rate of change in total chlorine concentration, w' is the residual chloramine concentration, and "x" is the residual chloramine concentration set-point; or (ii) o≤p and w'<x=add chlorine, where "o" is the rate of change in oxidation-reduction potential, "p" is the set rate of change in oxidation-reduction potential, w' is the residual chloramine concentration, and "x" is the residual chloramine concentration set-point. Thus, the programming instructions can include at least one of the above algorithms that, when satisfied, will cause the controller 40 to continue to automatically engage (or control) a supply of chlorine to add chlorine to the body of water 12.

Further, the method step of continually adding chlorine and ammonia at a weight ratio of chlorine to ammonia of greater than 5:1 when the set rate of change in total chlorine concentration and/or oxidation-reduction potential is achieved can be controlled by the following example algorithms: (i) w≥y and w'<x=add chlorine and ammonia at a weight ratio of chlorine to ammonia of greater than 5:1, where "w" is the rate of change in total chlorine concentration, "y" is the set rate of change in total chlorine concentration, w' is the residual chloramine concentration, and "x" is the residual chloramine concentration set-point; or (ii) o≤p and w'<x=add chlorine and ammonia at a weight ratio of chlorine to ammonia of greater than 5:1, where "o" is the rate of change in oxidation-reduction potential, "p" is the set rate of change in oxidation-reduction potential, w' is the residual chloramine concentration, and "x" is the residual chloramine concentration set-point. Thus, the programming instructions can include at least one of the above algorithms that, when satisfied, will cause the controller 40 to continue to automatically engage (or control) a supply of chlorine and ammonia to add chlorine and ammonia to the body of water 12 at a weight ratio of chlorine to ammonia of greater than 5:1.

Further, if the residual chloramine concentration in a subsequent additional water sample is determined to be at or above the predetermined chloramine concentration target level, the programming instructions will cause the controller 40 to stop the supply of chlorine, and optionally ammonia when also supplied, into the body of water 12.

In some preferred and non-limiting embodiments or aspects, the method step of stopping the supply of chlorine is controlled by the following algorithm: w≤x=stop the supply of chlorine, where "w" is the residual chloramine concentration determined in a water sample, and "x" is the residual chloramine concentration set-point. Further, the method step of stopping the supply of chlorine and ammonia when both supplied is controlled by the following algorithm: w≥x=stop the supply of chlorine and ammonia, where "w" is the residual chloramine concentration determined in a water sample, and "x" is the residual chloramine concentration set-point. Thus, the programming instructions can include the above algorithm that, when satisfied, will cause the controller 40 to stop automatically engaging (or controlling) a supply of chlorine and ammonia, and therefore, stop adding chlorine and ammonia to the body of water 12.

In some preferred and non-limiting embodiments or aspects, different programming algorithms are used to control when the supply of chlorine, and optionally ammonia when also supplied, into the body of water 12 is stopped. For instance, the method step of stopping the supply of chlorine can be controlled by the following algorithm: w>[(t)(x)]=stop the supply of chlorine, where "w" is the residual chloramine concentration determined in the second water sample, "t" is a percentage selected within a range of 101% to 110%, and "x" is the residual chloramine concentration set-point. In addition, the method step of stopping the supply of chlorine and ammonia can be controlled by the following algorithm: w>[(t)(x)]=stop the supply of chlorine and ammonia, where "w" is the residual chloramine concentration determined in the second water sample, "t" is a percentage selected within a range of 101% to 110%, and "x" is the residual chloramine concentration set-point.

It is appreciated that the predetermined chloramine concentration target level for stopping the addition of chlorine, and optionally ammonia when also supplied, can be based on a total chlorine concentration target level. As such, the predetermined chloramine concentration target level used in the previously described method steps and algorithms for stopping the addition of chlorine, and optionally ammonia when also supplied, can be based on a predetermined total chlorine concentration set-point or a percentage of the predetermined total chlorine concentration set-point. In such embodiments, the residual chloramine concentration is based on and/or determined from the residual total chlorine concentration in the water samples.

Figure 3:
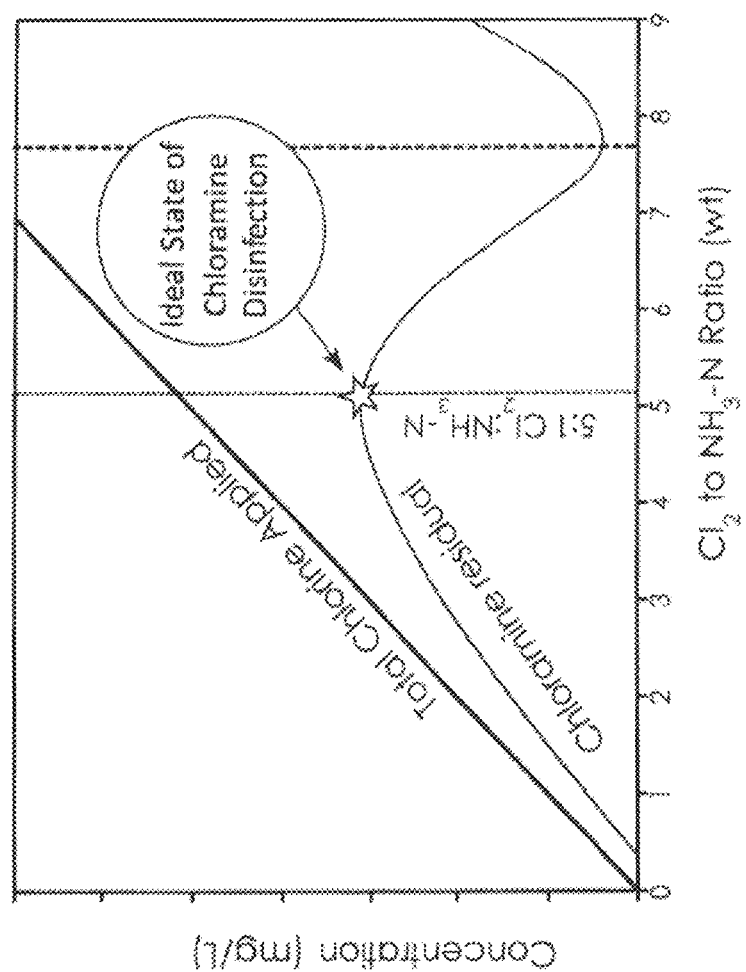
FIG. 3 is a chloramine breakpoint curve.

The method of the present invention works in accordance with the chloramine breakpoint curve, shown in FIG. 3. In particular, the previously described steps are used to achieve and maintain an ideal state of monochloramine disinfectant by predicting where the chloramine concentration in the body of water 12 resides along the breakpoint curve, the rate at which chloramine concentration is increasing and decreasing in the body of water 12 over time, and adjusting the input of chlorine or chlorine and ammonia into the body of water 12 to achieve and maintain a position at or near the ideal state. As shown in FIG. 3, the ideal state (i.e., the maximum monochloramine concentration obtainable in a body of water 12) is typically achieved at a weight ratio of chlorine ($Cl_2$) to ammonia-nitrogen ($NH_3-N$) of 5:1.

Figure 4:
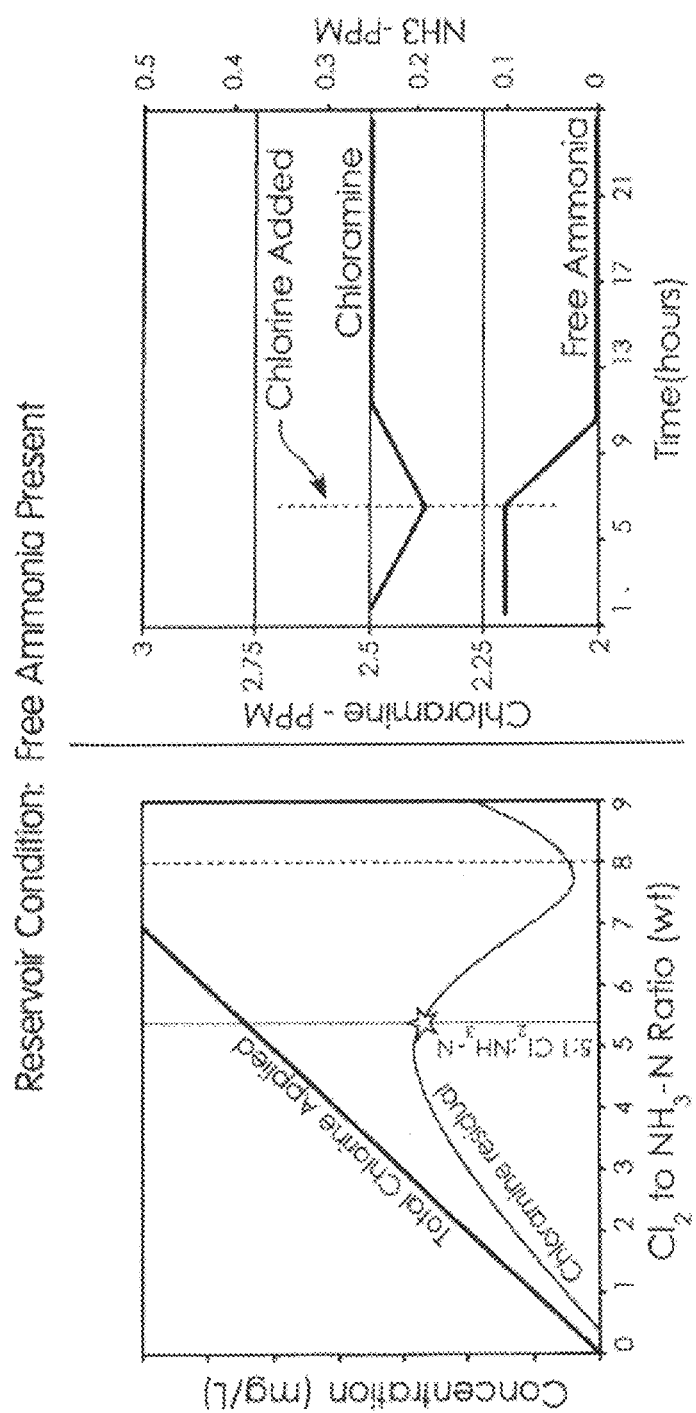
FIG. 4 depicts graphs illustrating the addition of chlorine in the presence of free ammonia to generate chloramine.
Figure 5:
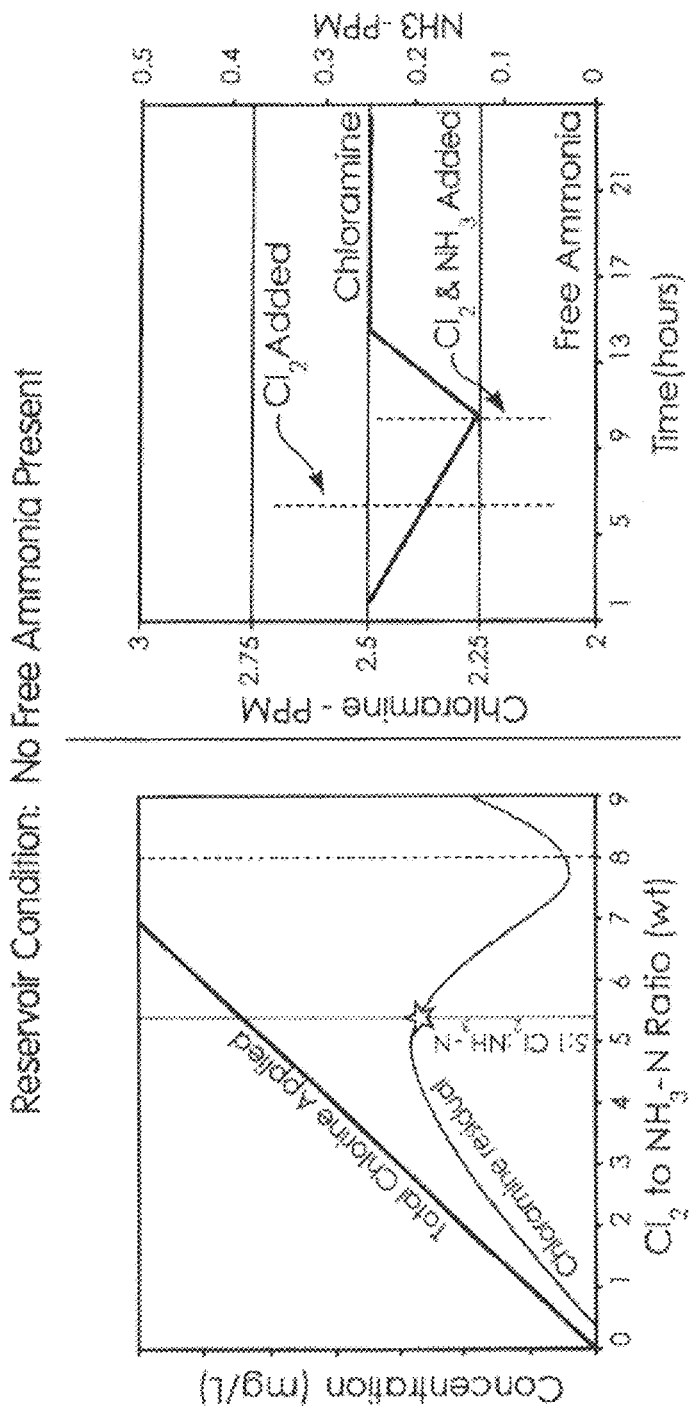
FIG. 5 depicts graphs illustrating the addition of chlorine and ammonia in the absence of free ammonia to generate chloramine.

Referring to FIGS. 4 and 5, and in one preferred and non-limiting embodiment or aspect, the method includes at least two modes, or stages, in view of the chloramine breakpoint curve. In the first mode shown in FIG. 4, it is assumed that free ammonia is present in the body of water 12. During the first mode, water samples are periodically drawn from the body of water 12 and analyzed to determine the chloramine concentration. In one preferred and non-limiting embodiment or aspect, this determination is accomplished by measuring the total chlorine present in the sample using a total chlorine analyzer, such as the total chlorine analyzer commercially available from ProMinent Fluid Controls, Inc. of Pittsburgh, Pa. If the system 10 determines that the total chlorine levels measured are in decline, the controller 40 can be configured to engage (or control) the treatment tubes 22 or 24 to add chlorine, and optionally ammonia at a weight ratio of chlorine to ammonia of greater than 5:1, to the body of water 12. Newly added chlorine will react with the free ammonia to generate chloramine, thus increasing the concentration of chloramine in the body of water 12 and reducing the concentration of free ammonia, as reflected in FIG. 4. Once the residual chloramine concentration target level is reestablished, or established in the first instance, the addition of chlorine, and optionally ammonia when also supplied, can cease.

In the second mode or stage of the control method as shown in FIG. 5, no free ammonia is present in the body of water 12. Because no free ammonia is present, the addition of chlorine, and optionally ammonia at a weight ratio of chlorine to ammonia of greater than 5:1, in response to a recognized drop in the chloramine concentration will result not in an upswing (or increase) in the chloramine concentration, as in the first mode described above, but rather in a further reduction in the chloramine concentration. This is caused by the absence of a sufficient amount of free ammonia in the body of water 12, which precludes the formation of chloramine through a reaction between the added chlorine and free ammonia. If, after the addition of chlorine, and optionally ammonia at a weight ratio of chlorine to ammonia of greater than 5:1, in the first mode, the chloramine concentration does not increase after a sufficient amount of time and the rate of change in the total concentration concentration is below the set rate of change in total chlorine concentration or the rate of change in the oxidation-reduction potential is above the set rate of change in oxidation-reduction potential, the system 10 can conclude that a sufficient amount of free ammonia is absent from the body of water 12. In response, the controller 40 is configured to engage (or control) a source of chlorine and a source of ammonia to inject into the body of water 12 at a weight ratio of chlorine to ammonia of 5:1 or less, as reflected in FIG. 5. The ammonia and chlorine at a weight ratio of chlorine to ammonia of 5:1 or less can continue being added until analysis of water samples extracted from the body of water 12 determines that the residual chloramine concentration target level has been reestablished (or established). In some preferred and non-limiting embodiments or aspects, ammonia and chlorine are added at a weight ratio of chlorine to ammonia of 5:1 or less for a period a time and then stopped to allow for a low concentration of free ammonia without achieving the residual chloramine concentration target level.

It is appreciated that the second mode is initiated by the ability of the system 10 to predict the location of the chloramine reaction on the break point curve and the rate at which the chloramine concentration is increasing or decreasing. For instance, if the measured total chlorine residual concentration continues to decrease as chlorine, and optionally ammonia at a weight ratio of chlorine to ammonia of greater than 5:1, is added or if the oxidation-reduction potential continues to increase as chlorine, and optionally ammonia at a weight ratio of chlorine to ammonia of greater than 5:1, is added, the system 10 can conclude that a sufficient amount of free ammonia is not present and that the residual chloramine concentration is decreasing past the ideal state shown in FIG. 5. As a result, the second mode is initiated and the controller 40 will add chlorine and ammonia into the body of water 12 at a weight ratio of chlorine to ammonia of 5:1 or less.

In some preferred and non-limiting embodiments or aspects, the second mode or stage of the control method is determined without engaging the supply of chlorine, or chlorine and ammonia at a weight ratio of chlorine to ammonia of greater than 5:1, when the total chlorine levels measured are in decline, the rate of change in the total concentration is below the set rate of change in total chlorine concentration, and the rate of change in the oxidation-reduction potential is above the set rate of change in oxidation-reduction potential. In response, the controller 40 is configured to engage (or control) a source of chlorine and a source of ammonia to inject into the body of water 12 at a weight ratio of chlorine to ammonia of 5:1 or less.

It is appreciated that the rate of change in total chlorine concentration and/or oxidation-reduction potential can be used to determine the chloramine concentration such as the concentration of monochloramine, di-chloramine, or the like. For instance, and as previously explained, the rate of change in total chlorine concentration and/or oxidation-reduction potential can be used to determine if the chemicals in the body of water are in a state of monochloramine or di-chloramine, which can then be used to determine chlorine and ammonia feed rate and/or a ratio of chlorine to ammonia that should be supplied to the body of water 12.

As indicated, any of the previously described method steps, or combination of steps, can be used to establish, reestablish, and maintain a desired residual chloramine level within the body of water 12. In one preferred and non-limiting embodiment or aspect, at least one of the previously described method steps, or combination of steps, are used to establish or reestablish a predetermined chloramine concentration target level. After the desired predetermined chloramine concentration target level is established or reestablished to complete a first treatment cycle, a different algorithm can be used to reestablish the desired residual chloramine concentration in subsequent treatment cycles.

In one preferred and non-limiting embodiment or aspect, after a first treatment cycle is completed, the controller 40 is programmed to only engage (or control) a supply of chlorine and a supply of ammonia to add both chlorine and ammonia to the body of water 12 at a weight ratio of chlorine to ammonia of 5:1 or less in order to reestablish the predetermined chloramine concentration target level. Thus, in such embodiments, chlorine alone, or chlorine and ammonia at a weight ratio of chlorine to ammonia of greater than 5:1, is not added to the body of water 12 in a second treatment cycle. For example, after a first treatment cycle is completed, the programming instructions of the computer-readable storage mediums can be configured to cause the controller 40 to automatically add both chlorine and ammonia to the body of water 12 at a weight ratio of chlorine to ammonia of 5:1 or less when the residual chloramine concentration in a water sample is determined to be below the predetermined chloramine concentration target level.

In some preferred and non-limiting embodiments or aspects, the previously described method step of adding ammonia and chlorine into the body of water 12 in a second treatment cycle is controlled by the following algorithm: $y'<x'$=add chlorine and ammonia at a weight ratio of chlorine to ammonia of 5:1 or less, where "y'" is the residual chloramine concentration determined in a water sample of the second treatment cycle and "x'" is the residual chloramine concentration set-point. Thus, the programming instructions can include the above algorithm for use in a second treatment cycle that, when satisfied, will cause the controller 40 to automatically engage (or control) a supply of chlorine and a supply of ammonia to add both chlorine and ammonia to the body of water 12 at a weight ratio of chlorine to ammonia of 5:1 or less.

The method can also use a chloramine concentration percentage of the residual chloramine concentration set-point to determine when to add both chlorine and ammonia to the body of water 12 at a weight ratio of chlorine to ammonia of 5:1 or less in a second treatment cycle. The chloramine concentration percentage can include, for example, a percentage selected within a range of 99% to 80% of the residual chloramine concentration set-point.

In some preferred and non-limiting embodiments or aspects, the previously described method step of adding chlorine and ammonia into the body of water 12 at a weight ratio of chlorine to ammonia of 5:1 or less in a second treatment cycle based on a chloramine concentration percentage is controlled by the following algorithm: $y'<[(a')(x')]$=add chlorine and ammonia at a weight ratio of chlorine to ammonia of 5:1 or less, where "y'" is the residual chloramine concentration determined in a water sample of the second treatment cycle, "a'" is a percentage selected within a range of 99% to 80%, and "x'" is the residual chloramine concentration set-point. Thus, the programming instructions can include the above algorithm for use in a second treatment cycle that, when satisfied, will cause the controller 40 to automatically engage (or control) a supply of chlorine and a supply of ammonia to add both chlorine and ammonia to the body of water 12 at a weight ratio of chlorine to ammonia of 5:1 or less.

Chlorine and ammonia are added to the body of water 12 until a subsequently obtained water sample is determined to be at or above the residual chloramine concentration set-point or above a particular percentage of the residual chloramine concentration set-point, at which point the programming instructions will cause the controller 40 to stop the supply of chlorine and ammonia into the body of water 12.

The predetermined chloramine concentration target level for adding chlorine and ammonia in a second or subsequent treatment cycle can be based on a total chlorine concentration target level. In such embodiments, the residual chloramine concentration is based on and/or determined from the residual total chlorine concentration in the water samples.

After reestablishing the predetermined chloramine concentration target level in the second treatment cycle, the programming instructions will cause the controller 40 to revert back to the original algorithm or cause the controller 40 to continue to use the modified algorithm. It is appreciated that the controller 40 can be programmed to alternate between different algorithms for any desired number of treatment cycles. For example, in a first treatment cycle, the controller 40 can be programmed to supply chlorine alone, or chlorine and ammonia at a weight ratio of greater than 5:1, in a first step, and optionally, both chlorine and ammonia at a weight ratio of chlorine to ammonia of 5:1 or less in a second step in order to establish the predetermined chloramine concentration target level. Then, after a first treatment cycle is completed, the controller 40 can be programmed to supply both chlorine and ammonia only at a weight ratio of chlorine to ammonia of 5:1 or less in order to reestablish the predetermined chloramine concentration target level in the next three treatment cycles. Finally, to reestablish the residual chloramine concentration set-point in a fifth treatment cycle, the controller 40 can be programmed to use the original algorithm and supply chlorine alone, or chlorine and ammonia at a weight ratio of greater than 5:1, in a first step, and optionally, both chlorine and ammonia at a weight ratio of chlorine to ammonia of 5:1 or less in a second step.

The feed rate of chlorine and/or ammonia in any of the previously described steps can be determined from the reservoir 14 water volume and dwell time. As used herein, "dwell time" refers to the rate at which water volume changes in the reservoir 14. The feed rate of the chlorine and ammonia can also be controlled by the speed at which the metering pumps distribute the chlorine and ammonia into the body of water 12. For example, the metering pumps can distribute chlorine and ammonia at a maximum speed rate. The metering pumps can also be reduced to half (i.e., 50%) of the maximum speed rate to adjust the feed rate of chlorine and ammonia.

The method of automatically controlling chloramine concentration described herein allows for a desired amount of chloramine in a body of water 12 to be effectively maintained without directly measuring or initially adding free ammonia. The system and method can also be used to respond to an adjustment, such as an increase, in the target chloramine concentration.

Figure 6:
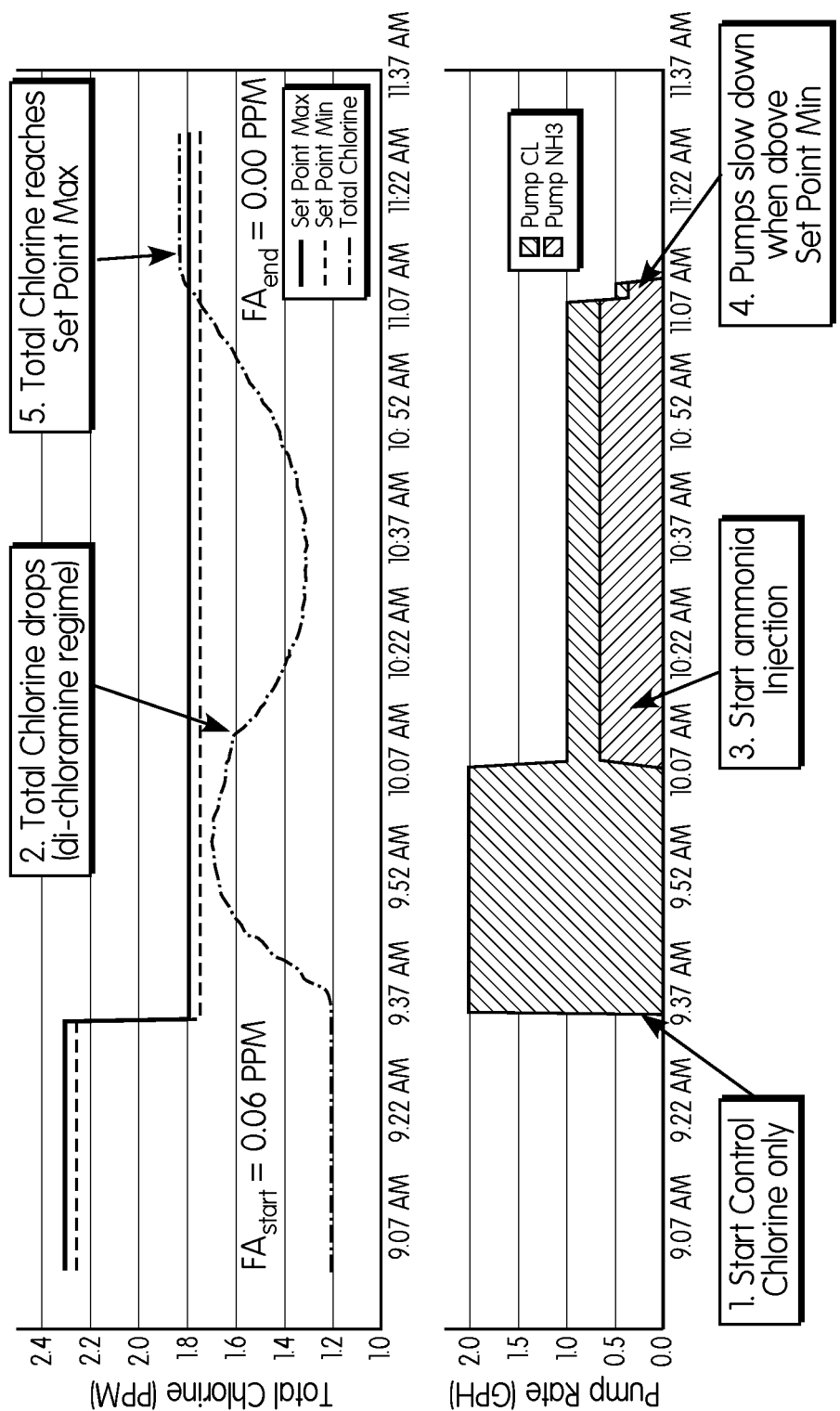
FIG. 6 is a graph of the residual chloramine concentration and addition of chlorine and ammonia using a process according to the principles of the present invention.
Figure 7:
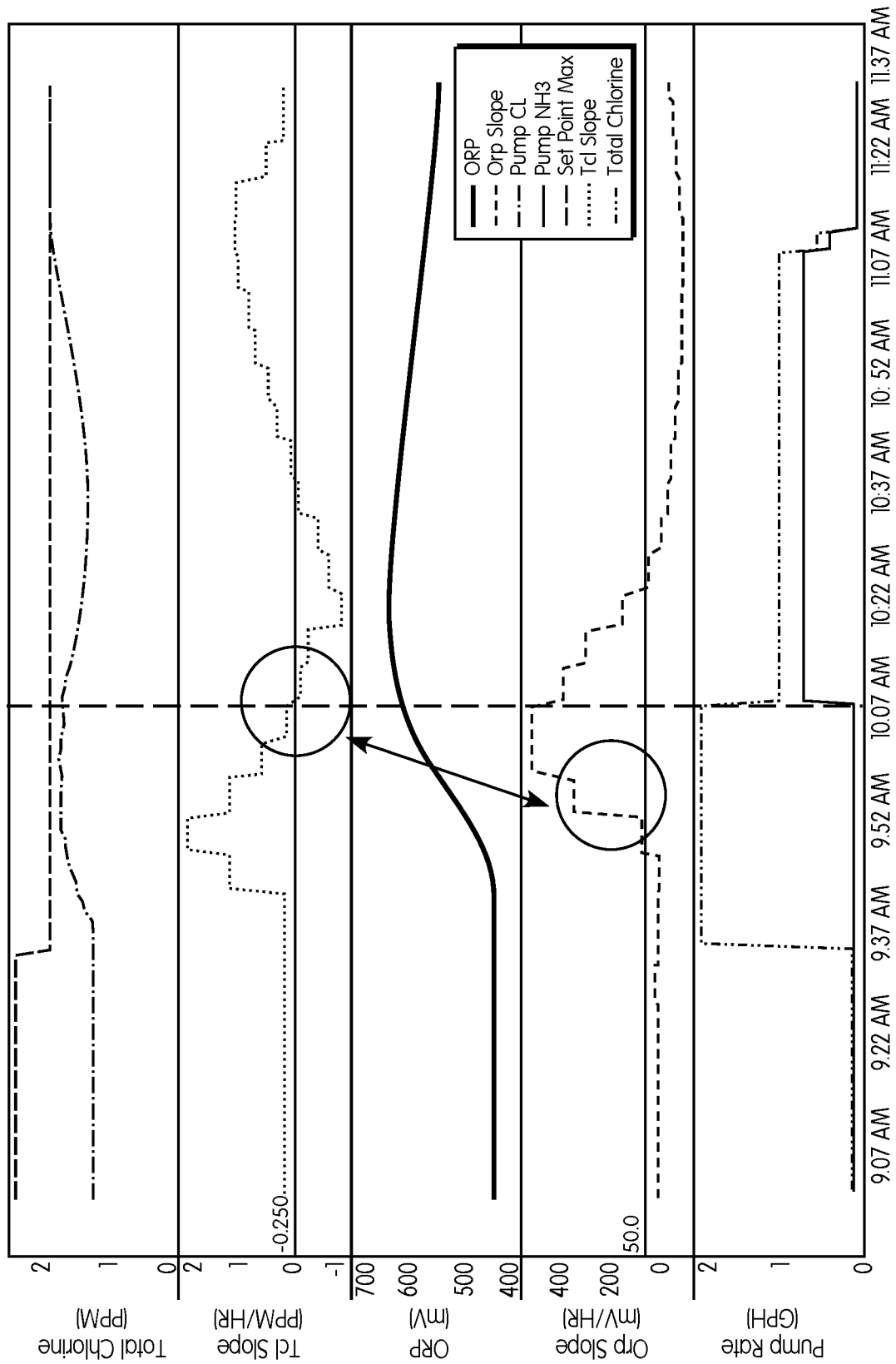
FIG. 7 is a graph of the total chlorine, oxidation-reduction potential, rate of change of total chlorine concentration, rate of change of oxidation-reduction potential, and the feed rate of chlorine and ammonia using a process according to the principles of the present invention.

FIGS. 6 and 7 show the total chlorine concentration, the rate of change in total chlorine concentration, the oxidation-reduction potential, and the rate of change in oxidation-reduction potential in a water storage reservoir that utilized the treatment delivery system 10 and the method of automatically controlling chloramine concentration according to the present invention. The treatment delivery system 10 was programmed to add chlorine when the residual total chlorine concentration was below the predetermined total chlorine concentration target level. Further, while adding chlorine, the treatment delivery system 10 was also programmed to add chlorine and ammonia at a weight ratio of chlorine to ammonia of 5:1 or less when the rate of change in the total chlorine concentration is below the set rate of change in total chlorine concentration or the rate of change in the oxidation-reduction potential is above the set rate of change in oxidation-reduction potential.

As shown in FIG. 6, the system was turned on and hypochlorite was added to the body of water 12 after determining that a water sample had a residual total chlorine concentration below the predetermined total chlorine concentration set-point. After adding the chlorine, the rate of change in total chlorine concentration and the rate of change in oxidation-reduction potential was calculated throughout the process. Referring to FIG. 7, the rate of change in residual total chlorine concentration and the rate of change in oxidation-reduction potential obtained over a specified period of time did not achieve the set rate of change in total chlorine concentration and the set rate of change in oxidation-reduction potential. As a result, and as shown in FIGS. 6 and 7, the supply of ammonia was engaged along with the supply of chlorine at a weight ratio of chlorine to ammonia of 5:1 or less.

Moreover, the predetermined chloramine concentration target level included a minimum predetermined total chlorine concentration set-point and a maximum predetermined total chlorine concentration set-point. Once the minimum predetermined total chlorine concentration set-point was reached, the feed rate of the chlorine and ammonia was decreased. Further, once the maximum predetermined total chlorine concentration set-point was reached, the supply of chlorine and the ammonia into the body of water 12 was stopped.

Whereas particular embodiments of this invention have been described above for purposes of illustration, it will be evident to those skilled in the art that numerous variations of the details of the present invention may be made without departing from the invention as defined in the appended claims.

The invention claimed is:

1. A method of automatically controlling chloramine concentration in a body of water contained in a reservoir, the method comprising:
   a) determining residual chloramine concentration in a water sample obtained from the body of water;
   b) determining at least one of the following when the residual chloramine concentration is below a predetermined target chloramine concentration level:
      i) an average rate of change in total chlorine concentration based on total chlorine concentrations of water samples obtained from the body of water; and
      ii) an average rate of change in oxidation-reduction potential based on oxidation-reduction potentials of water samples obtained from the body of water; and
   c) automatically engaging a supply of ammonia and a supply of chlorine to add both ammonia and chlorine to the body of water at a weight ratio of chlorine to ammonia of 5:1 or less when:
      i) the average rate of change in total chlorine concentration is below a set rate of change in total chlorine concentration;
      ii) the average rate of change in oxidation-reduction potential is above a set rate of change in oxidation-reduction potential; or
      iii) the average rate of change in total chlorine concentration is below a set rate of change in total chlorine concentration and the average rate of change in oxidation-reduction potential is above a set rate of change in oxidation-reduction potential.

2. The method of claim 1, wherein the average rate of change in total chlorine concentration is determined in step b), and wherein ammonia and chlorine are both added to the body of water at a weight ratio of chlorine to ammonia of 5:1 or less in step c) when i) the average rate of change in total chlorine concentration is below the set rate of change in total chlorine concentration.

3. The method of claim 1, wherein the average rate of change in oxidation-reduction potential is determined in step b), and wherein ammonia and chlorine are both added to the body of water at a weight ratio of chlorine to ammonia of 5:1 or less in step c) when ii) the average rate of change in oxidation-reduction potential is above the set rate of change in oxidation-reduction potential.

4. The method of claim 1, wherein the average rate of change in total chlorine concentration and the average rate of change in oxidation-reduction potential is determined in step b), and wherein ammonia and chlorine are both added to the body of water at a weight ratio of chlorine to ammonia of 5:1 or less in step c) when iii) the average rate of change in total chlorine concentration is below the set rate of change in total chlorine concentration and the average rate of change in oxidation-reduction potential is above the set rate of change in oxidation-reduction potential.

5. The method of claim 1, further comprising automatically engaging a supply of chlorine to add chlorine only to the body of water if the residual chloramine concentration in the water sample obtained from the body of water in step a) is below the predetermined target chloramine concentration level.

6. The method claim 1, further comprising automatically engaging a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

7. The method of claim 6, wherein a feed rate of the chlorine and ammonia supplied to the body of water after step a) is different than a feed rate of the chlorine and ammonia supplied to the body of water in step c).

8. The method of claim 4, wherein the average rate of change in total chlorine concentration and the average rate of change in oxidation-reduction potential in step b) is determined when the supply of chlorine and ammonia are disengaged.

9. The method of claim 1, wherein the average rate of change in total chlorine concentration is determined by measuring the change in residual total chlorine concentration in consecutively obtained water samples over a fixed period of time, and
   wherein the average rate of change in oxidation-reduction potential is determined by measuring the change in oxidation-reduction potential in consecutively obtained water samples over a fixed period of time.

10. The method of claim 1, wherein, if the average rate of change in total chlorine concentration is determined to be at or above the set rate of change in total chlorine concentration, chlorine only is added to the body of water or chlorine and ammonia are added to the body of water at a weight ratio of chlorine to ammonia of greater than 5:1.

11. The method of claim 1, wherein, if the average rate of change in oxidation-reduction potential is determined to be at or below the set rate of change in oxidation-reduction potential, chlorine only is added to the body of water or chlorine and ammonia are added to the body of water at a weight ratio of chlorine to ammonia of greater than 5:1.

12. The method of claim 1, wherein the supply of chlorine and the supply of ammonia are added to the body of water during step c) until a subsequently obtained water sample is determined to be at or above the predetermined target chloramine concentration level.

13. The method of claim 12, wherein the predetermined target chloramine concentration level comprises a minimum predetermined total chlorine concentration set-point and a maximum predetermined total chlorine concentration set-point, and
   wherein the feed rate of the chlorine and/or the ammonia is decreased when the total chlorine concentration is at or above the minimum predetermined total chlorine concentration set-point and below the maximum predetermined total chlorine concentration set-point, and
   wherein the supply of chlorine and the supply of ammonia are disengaged when the total chlorine concentration is at or above the maximum predetermined total chlorine concentration set-point.

14. The method of claim 1, wherein the feed rate of the chlorine and ammonia are determined by reservoir water volume and dwell time.

15. The method of claim 1, wherein the residual chloramine concentration is based on a residual total chlorine concentration and the predetermined target chloramine concentration level is based on a target total chlorine concentration level.

16. The method of claim 1, wherein the oxidation-reduction potentials of the samples are determined by measuring millivolts of the water samples.

17. A treatment delivery system for automatically controlling chloramine concentration in a body of water contained in a reservoir comprising:
 a chemical dosing assembly;
 a water sampling assembly configured to extract water sample from the body of water at different points in time;
 one or more analyzers in fluid communication with the water sampling assembly and configured to determine at least total chlorine concentration, and optionally, oxidation-reduction potential in the water samples;
 a controller in operable communication with the one or more analyzers; and
 one or more computer-readable storage mediums in operable communication with the controller and containing programming instructions that, when executed, cause the controller to:
 a) determine residual chloramine concentration in a water sample obtained from the body of water;
 b) determine at least one of the following when the residual chloramine concentration is below a predetermined target chloramine concentration level:
  i) an average rate of change in total chlorine concentration based on residual total chlorine concentrations of water samples obtained from the body of water; and
  ii) an average rate of change in oxidation-reduction potential based on oxidation-reduction potentials of water samples obtained from the body of water; and
 c) automatically engage a supply of ammonia and a supply of chlorine to add both ammonia and chlorine to the body of water at a weight ratio of chlorine to ammonia of 5:1 or less when:
  i) the average rate of change in total chlorine concentration is below a set rate of change in total chlorine concentration while chlorine is added to the body of water;
  ii) the average rate of change in oxidation-reduction potential is above a set rate of change in oxidation-reduction potential while chlorine is added to the body of water; or
  iii) the average rate of change in total chlorine concentration is below a set rate of change in total chlorine concentration and the average rate of change in oxidation-reduction potential is above a set rate of change in oxidation-reduction potential.

18. The system of claim 17, wherein the chemical dosing assembly is at least partially submerged in the body of water.

19. The system of claim 17, wherein the computer-readable storage mediums in operable communication with the controller further comprise programming instructions that, when executed, cause the controller to automatically engage a supply of chlorine to add chlorine only to the body of water if the residual chloramine concentration in the water sample obtained from the body of water in step a) is below the predetermined target chloramine concentration level.

20. The system of claim 17, wherein the computer-readable storage mediums in operable communication with the controller further comprise programming instructions that, when executed, cause the controller to automatically engage a supply of chlorine and a supply of ammonia to add both chlorine and ammonia to the body of water at a weight ratio of chlorine to ammonia of greater than 5:1 if the residual chloramine concentration in the water sample obtained from the body of water in step a) is below the predetermined target chloramine concentration level.

* * * * *